(12) United States Patent
Graumann et al.

(10) Patent No.: US 8,693,622 B2
(45) Date of Patent: Apr. 8, 2014

(54) X-RAY METHOD AND X-RAY SYSTEM FOR MERGING X-RAY IMAGES AND DETERMINING THREE-DIMENSIONAL VOLUME DATA

(75) Inventors: Rainer Graumann, Höchstadt (DE); Anna Jerebko, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 93 days.

(21) Appl. No.: 13/442,086

(22) Filed: Apr. 9, 2012

(65) Prior Publication Data

US 2012/0257714 A1    Oct. 11, 2012

(30) Foreign Application Priority Data

Apr. 7, 2011    (DE) .......................... 10 2011 006 991

(51) Int. Cl.
*A61B 6/03* (2006.01)
*G01N 23/04* (2006.01)

(52) U.S. Cl.
USPC ............................................. 378/19; 378/62

(58) Field of Classification Search
USPC ....................... 378/196, 197, 62, 4, 39, 25, 19
See application file for complete search history.

(56) References Cited

U.S. PATENT DOCUMENTS

| 7,073,939 | B2 * | 7/2006 | Spahn ........................... 378/196 |
| 7,620,144 | B2 * | 11/2009 | Bodduluri ....................... 378/41 |
| 7,634,056 | B2 * | 12/2009 | Graumann et al. ............. 378/62 |
| 7,796,723 | B2 | 9/2010 | Haerer et al. |

(Continued)

FOREIGN PATENT DOCUMENTS

| DE | 102006036327 A1 | 2/2008 |
| DE | 102007026115 A1 | 12/2008 |

(Continued)

OTHER PUBLICATIONS

Oppelt, "Imaging Systems for Medical Diagnostics, Fundamentals, Technical Solutions and Applications for Systems Applying Lonizing Radiation, Nuclear Magnetic Resonance and Ultrasound", Nov. 2005, pp. 65-82, Publicis Corporate Publishing, Erlangen, Germany.

(Continued)

*Primary Examiner* — Irakli Kiknadze
(74) *Attorney, Agent, or Firm* — Laurence A. Greenberg; Werner H. Stemer; Ralph E. Locher

(57) ABSTRACT

Three-dimensional image information is generated of a body part that is larger than the visual field of an X-ray machine. An X-ray source and an X-ray detector are disposed at a first position such that the X-ray source and the X-ray detector can record a first projection image of at least a first section of a body part. Then the first projection image is recorded. The X-ray source and the X-ray detector are next disposed at a second position such that the X-ray source and the X-ray detector can record a second projection image of at least a second section of the body part. The second section partially overlaps the first section. The first and second projection images are merged to form a projected image. A three-dimensional volume of the body part is reconstructed from the plurality of projection images.

18 Claims, 2 Drawing Sheets

(56) References Cited

U.S. PATENT DOCUMENTS

| | | |
|---|---|---|
| 2005/0133708 A1* | 6/2005 | Eberhard et al. .............. 250/234 |
| 2008/0219567 A1* | 9/2008 | Claus et al. ................... 382/232 |
| 2008/0304617 A1 | 12/2008 | Brunner et al. |
| 2010/0310141 A1 | 12/2010 | Wilson |
| 2011/0085637 A1 | 4/2011 | Boese et al. |
| 2011/0188726 A1 | 8/2011 | Nathaniel et al. |

FOREIGN PATENT DOCUMENTS

| | | |
|---|---|---|
| EP | 2315178 A1 | 4/2011 |
| WO | 2007058918 A1 | 5/2007 |
| WO | 2009153789 A1 | 12/2009 |

OTHER PUBLICATIONS

Oppelt, "Imaging Systems for Medical Diagnostics, Fundamentals, Technical Solutions and Applications for Systems Applying Lonizing Radiation, Nuclear Magnetic Resonance and Ultrasound", Nov. 2005, pp. 378-393, Publicis Corporate Publishing, Erlangen, Germany.

Oppelt, "Imaging Systems for Medical Diagnostics, Fundamentals, Technical Solutions and Applications for Systems Applying Lonizing Radiation, Nuclear Magnetic Resonance and Ultrasound", Nov. 2005, pp. 214-228 and pp. 230-241, Publicis Corporate Publishing, Erlangen, Germany.

German Patent and Trademark Office, Office Action, Dated Feb. 3, 2012.

\* cited by examiner

X-RAY METHOD AND X-RAY SYSTEM FOR MERGING X-RAY IMAGES AND DETERMINING THREE-DIMENSIONAL VOLUME DATA

CROSS-REFERENCE TO RELATED APPLICATION

This application claims the priority, under 35 U.S.C. §119, of German patent application No. DE 10 2011 006 991.7, filed Apr. 7, 2011; the prior application is herewith incorporated by reference in its entirety.

BACKGROUND OF THE INVENTION

Field of the Invention

During diagnosis or an operation the surgeon wishes to receive image information about the inside of an operation site. X-ray systems having a so-called C-arm are used for this purpose by way of example. To determine information about the inside of the operation site the C-arm is pivoted into different positions and following pivoting a projection image is created in this position by way of X-ray irradiation. The image data obtained in the process illustrates the attenuation of an X-ray beam as it passes through the tissue during the respective projection. Sectional images can be reconstructed by way of imaging methods which supply the operator with three-dimensional image information about individual layers of the inside of the patient or of the operation site.

In a typical X-ray system having a C-arm, an X-ray radiation source is arranged at the upper end of the C-arm and an X-ray radiation detector is arranged at the lower end of the C-arm. The C-arm is preferably constructed isocentrically and it is pivoted isocentrically. The C-arm is a semi-circle, wherein the X-ray radiation source and the X-ray radiation detector are arranged at opposing ends of the semi-circle. The X-ray radiation source and the X-ray radiation detector are arranged in such a way that the central beam of the beam cone of the X-ray radiation source always runs through the center of rotation of the axis of rotation of the C-arm. The C-arm can be pivoted about approximately 190°.

X-ray systems having a C-arm, three-dimensional reconstructions, tomosynthesis and phantom-based calibration of an X-ray system having a C-arm are described in Imaging Systems for Medical Diagnostics, Publicis Corporate Publishing, Erlangen, ISBN: 3-89578-226-2.

Unfortunately X-ray systems having a C-arm have a limited visual field, so it is not possible to X-ray larger body parts, by way of example the femur, with a single image.

SUMMARY OF THE INVENTION

It is accordingly an object of the invention to provide a X-Ray Process and X-Ray system for merging x-ray images and for determining three-dimensional volume data, which overcome the above-mentioned disadvantages of the heretofore-known devices and methods of this general type and which provides for an imaging method and an imaging system which are capable of X-raying a body part which is larger than a visual field of an X-ray system.

With the foregoing and other objects in view there is provided, in accordance with the invention, a method for generating a three-dimensional image formation of a body part that is larger than a visual field of an X-ray machine, the method comprising the following steps:

arranging an X-ray source and an X-ray detector at a first position such that the X-ray source and the X-ray detector can record a first projection image of at least a first section of a body part;

recording the first projection image;

arranging the X-ray source and the X-ray detector at a second position such that the X-ray source and the X-ray detector can record a second projection image of at least a second section of the body part, wherein the second section partially overlaps the first section; and reconstructing a three-dimensional volume of the body part from a plurality of projection images including the first projection image and the second projection image.

In other words, the objects of the invention are achieved with a method for creating an X-ray image of a body part which is larger than the visual field of an X-ray machine that comprises the step of arranging an X-ray source and an X-ray detector at a first position, so the X-ray source and the X-ray detector can record a first projection image of at least a first section of a body part. The first projection image is then recorded. The X-ray source and the X-ray detector are arranged at a second position such that the X-ray source and the X-ray detector can record a second projection image of at least a second section of the body part, wherein the second section partially overlaps the first section. The three-dimensional volume of the body part is reconstructed from the plurality of projection images. Image data for the three-dimensional volume is reconstructed. Algebraic or iterative reconstruction algorithms can be used in this connection. The first and second projection images can be merged to form a projected image.

A plurality of projection images of partially overlapping sections of the body part can be recorded on a line at a plurality of positions and the plurality of projection images can be merged to form one projected image. The line is preferably located on a flat plane. The plurality of positions is preferably and substantially situated on a straight line, e.g. on a straight line running parallel to the middle longitudinal axis of the patient or parallel to a longitudinal axis of a long bone (e.g. along the femur). Image acquisition is therefore significantly different from conventional image acquisition using conventional 3D C-arm imaging, in which the projection images—in contrast to the present invention—are obtained or acquired by means of rotation about the patient's body.

The step of arranging the X-ray source at the positions can include the translatory movement of a C-arm and of the X-ray source secured thereto and of the X-ray detector secured thereto. In addition the C-arm and the X-ray source secured thereto and the X-ray detector secured thereto can also be moved rotationally.

Two adjacent projection images preferably overlap by at least approximately 80%, preferably by at least approximately 90%, most preferably by at least approximately 95%. Therefore at least approximately five projection images, preferably at least approximately 10 projection images, more preferably at least approximately 20 projection images, are produced from each position of the body part. Preferably nine to 20 projections are recorded per voxel to be reconstructed. Each voxel to be reconstructed is recorded with a projection angle range of less than 180°. The projection geometry of each projected image is known, so the projection images may be reliably merged. The projections have a sliding visual field with an overlap of preferably at least approximately 90% between adjacent projections. Approximately 100 images can be recorded per 1 m. The projections are consequently cropped in the main axis of the long body part, by way of example of the femur. Each projection shows only one part of the femur in its longitudinal direction.

The plurality of positions at which one projection image each is produced is situated roughly on a straight line. A C-arm X-ray system can be linearly moved by way of example. The path used by the X-ray source and the X-ray detector during recording of the plurality of projection images is substantially flat and smooth. The algebraic or iterative reconstruction algorithms can be adapted so the flat trajectory of the X-ray source and the X-ray detector is taken into consideration when producing the projection image. A tomosynthesis reconstruction algorithm is suitable for this purpose, by way of example a filtered back projection according to Feldkamp. What are known as flat panel detectors are preferably used as X-ray detectors, and these are large-area detectors which have been developed for projection radiology. The X-ray source can emit a cone-shaped beam which in English is called a cone beam. A combination of this kind is also called a flat panel cone beam device. Image intensifier-based C-arms may also be used. The projection images produced therewith can be processed further using the above-mentioned Feldkamp algorithm, so tomosynthesis reconstruction of the volume, which has been acquired using the X-ray source and the X-ray detector, occurs.

The reconstruction algorithm reconstructs a three-dimensional volume, which illustrates the body part, from a limited number of projections which have been recorded using an X-ray source and an X-ray detector moved along a flat path. The reconstruction algorithm should be capable of minimizing artifacts outside of the plane and which have been produced by an incomplete angular range. The algorithm must also take account of the fact that the projections are cropped and the resolution in the Z direction (depth direction) is coarser over the volume to be reconstructed than the resolution in the X-direction or Y-direction. In particular the resolution in the Z-direction and the reconstructed slice thickness must be so high in especially relevant sections of the body part that a calculation of a projected image is possible from any other desired direction. During the examination of a femur the image resolution of the femoral head must be so good that calculation of the anteversion angle is possible.

Projection data of a volume unit of the body part can be acquired from at least two different angles by means of X-ray radiation of the X-ray source moved along a line to the X-ray detector moved along a line. The volume unit can be reconstructed on the basis of the projection images of the volume unit which are produced using X-ray radiation from at least two different angles.

It is therefore possible to reconstruct a three-dimensional volume even though the X-ray source and the X-ray detector and the C-arm are only moved along a line, by way of example a straight line, and not in the manner of an arc. It is also possible for the C-arm to be moved with the X-ray source and the X-ray detector translationally and rotationally.

According to the invention 3D information is reconstructed from the measured 2D information. The 3D-information obtained is available for all medically and operatively relevant tasks, so, for example, the leg length, leg rotation, leg axis (e.g. varus/valgus position) can be calculated with a high level of accuracy in order, by way of example, to improve the surgical result of an operation on the leg by reference to the measures of the respective other, healthy leg.

The emission area of the X-ray source can be smaller than the detection area of the X-ray detector. The X-ray source and the X-ray detector are successively arranged along a line opposite the volume unit of the body part such that the volume unit is irradiated with X-ray radiation emitted by the X-ray source from different angles. Since the X-ray source emits X-ray radiation in a cone-shaped region, the angle at which the X-ray radiation strikes the volume unit depends on the spacing of the volume unit from the X-ray source and from the centerpoint beam of the X-ray source. This effect is also called the parallax effect. The inventors have recognized that what is known as the parallax effect can be used to irradiate a volume unit from different angles and consequently be able to reconstruct three-dimensional image information of a plurality of volume units in a body part.

The length of the body part, length of a bone, rotation of a bone, rotation of a body part, rotation of elements of the bone with respect to each other, rotation of elements of the body part with respect to each other, axis positions of the bone or of parts of the body part and/or additional geometric relations of the body part, or parts thereof, with respect to each other can be determined from the reconstructed volume. The three-dimensional information of the body part and information derived therefrom can be determined intraoperatively, by way of example during an operation following a fracture.

The Z information can be determined per pixel on the basis of a plurality of X-ray beams by way of the parallax effect or parallax errors.

The method can produce a calculated projected image from the volume which has a different orientation to the recorded projection images. This makes it possible to examine the body part three-dimensionally even though only projection images along a straight line have been recorded. In particular the inventive method makes it possible to determine the anteversion angle of the femoral head and the leg length.

It is proposed that statistical models of the joints (by way of example of the hip joint, knee joint, foot, etc.) are used to increase the accuracy of the volume data. The statistical models are adapted to the reconstructed data for this purpose.

The body part mentioned in the introduction can be a bone, in particular the femur. The anteversion angle can be determined from the volume data and/or at least one calculated projected image.

The invention also discloses an imaging system which is designed to perform one of the above-mentioned method steps.

The invention also discloses a C-arm X-ray system comprising the imaging system.

The invention also discloses a computer program product which can be loaded in a memory of a computer or is loaded therein and comprises means which are set up to perform at least one of the preceding steps of the method.

Other features which are considered as characteristic for the invention are set forth in the appended claims.

Although the invention is illustrated and described herein as embodied in an X-ray method and X-ray system for merging X-ray images and determining three-dimensional volume data, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE INVENTION

Figure 1:
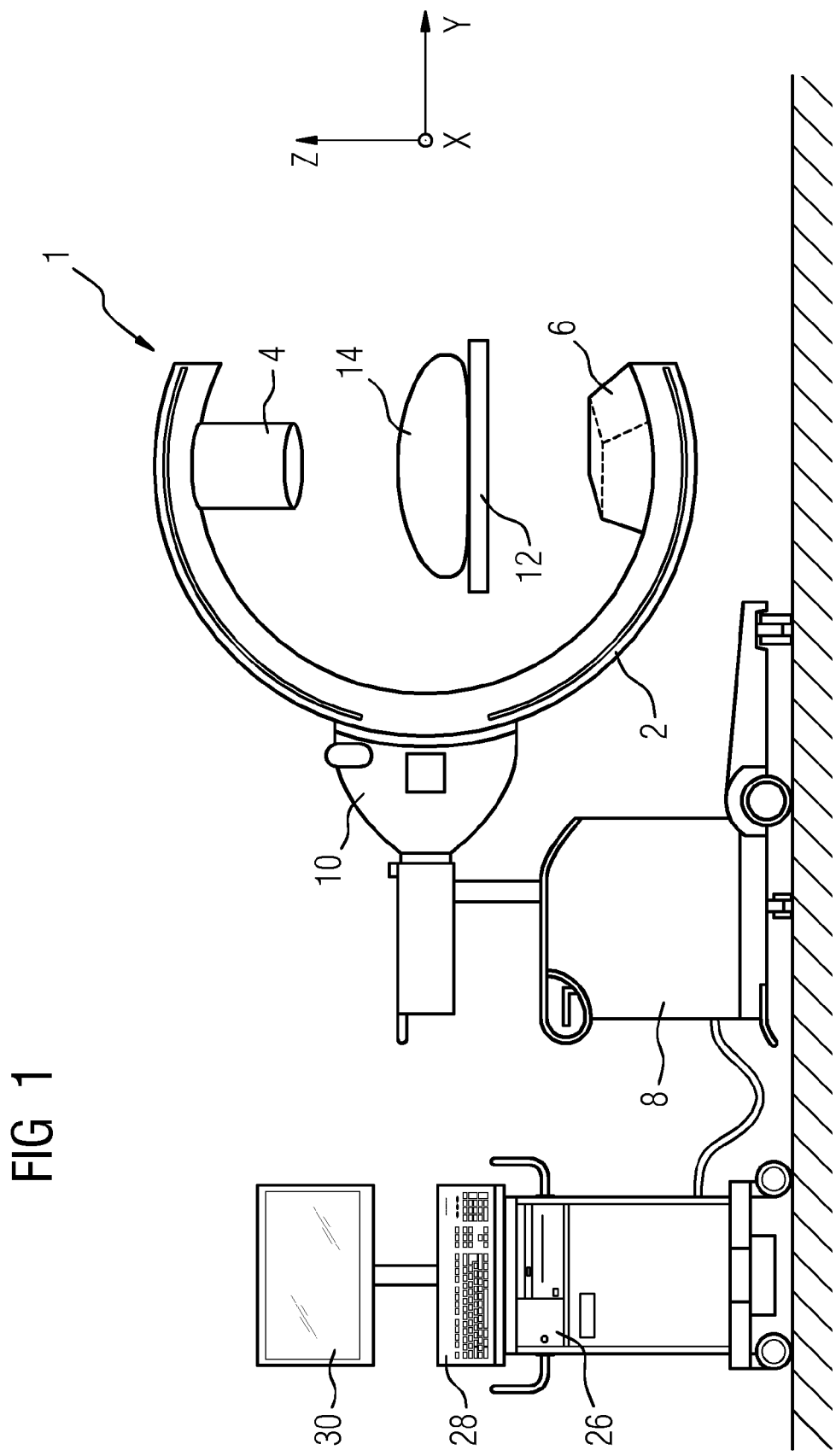
FIG. 1 is an elevation view of an exemplary C-arm X-ray system.

Referring now to the figures of the drawing in detail and first, particularly, to FIG. 1 thereof, there is shown an X-ray system 1 having a C-arm 2. The C-arm is, by way of example, an isocentric C-arm which is designed so as to be semicircular. An X-ray source 4 is arranged at the upper end of the C-arm and an X-ray detector 6 is arranged at the lower end of the C-arm. The C-arm 2 is pivotally arranged on a carriage 8 by means of a holding device 10. The carriage can be moved by way of wheels and the C-arm can consequently be pushed or moved to the desired application site. A patient 14 with the tissue to be examined is located on an operating table 12 made from an X-ray-transparent material, by way of example carbon.

Figure 2:
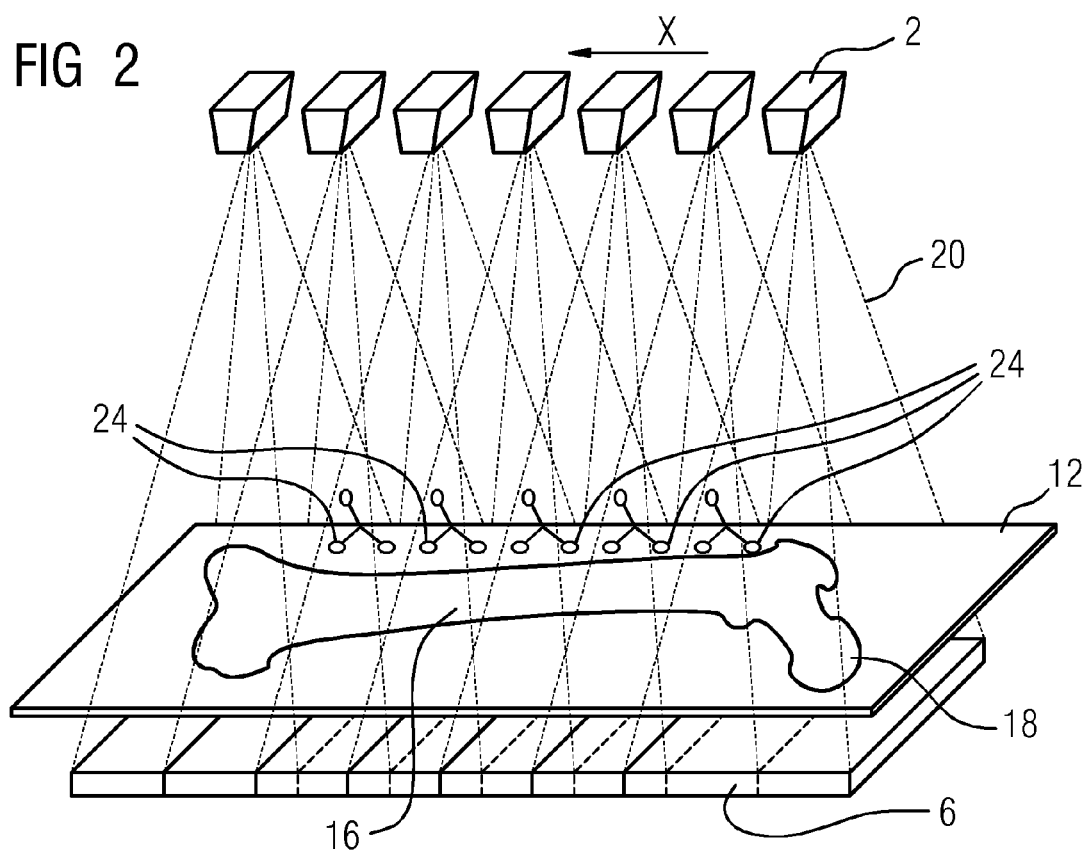
FIG. 2 shows a schematic illustration for producing the projection images.

FIG. 2 schematically shows a femur 16 to be examined, having a femoral head 18 which is located on the patient table 12. The femur is shown only schematically in FIG. 2, it is understood that additional patient tissue is arranged around the femur. Marking elements 24 with balls are also arranged on the patient table 12 and these serve to process the overlapping images into one image and to exactly determine the position relations and angle relations between the individual images. The X-ray source 2 emits a cone-shaped beam (cone beam). The X-ray detector 6 has a panel-type design (flat panel). The X-ray system shown in FIG. 2 is therefore a so-called flat panel cone beam X-ray system. The X-ray system is moved along axis X, so a plurality of overlapping projection images of the femur 16 and of the plurality of marking elements 24 are successively recorded by the X-ray source 2 and the X-ray detector 6. The X-ray source and the X-ray detector are moved for this purpose, and this is carried out by way of example such that the carriage 8 (see FIG. 1) of the C-arm 2 is moved along a straight line. The X-ray source 2 and the X-ray detector 6 are moved such that between five and 20 projection images are produced for each voxel. Preferably between approximately nine and approximately 20 projection images are produced per voxel.

Figure 3:
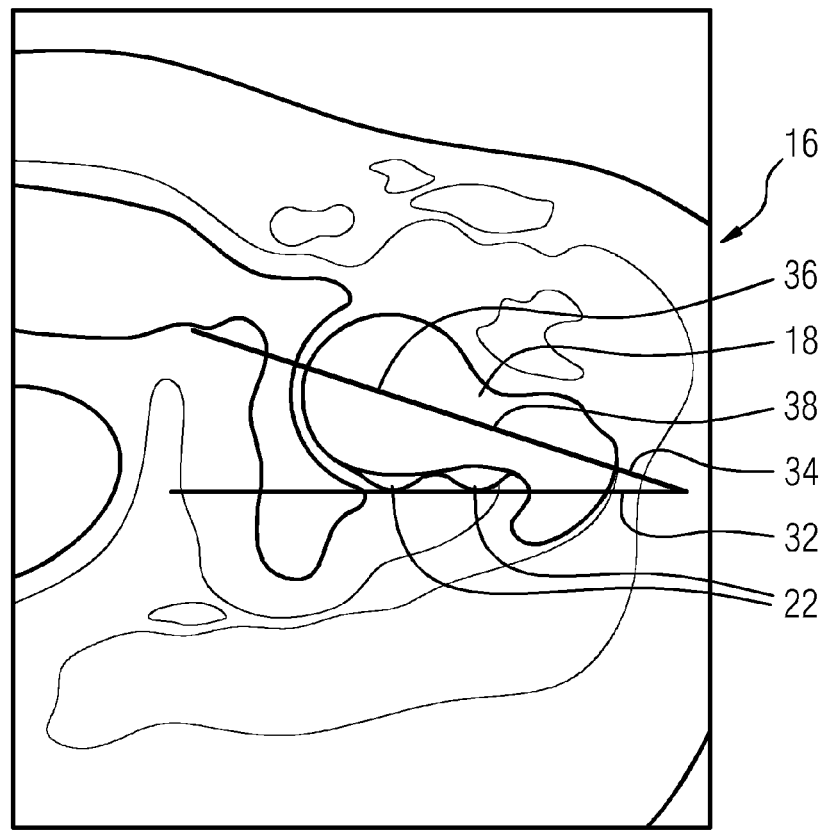
FIG. 3 shows a schematic view of a femoral head and the anteversion angle.

An imaging system 26 (see FIG. 1) produces a merged projection image from the plurality of projection images. Characteristic features or projection geometries are extracted in each individual projected image in this connection to produce the combined projection image of the femur 16. The imaging system 26 can also use the pictures of the marking elements 24 as reference geometries to produce the combined projection image of the femur 16. The bone axis (varus position or valgus position) can be determined from this combined projection image of the femur 16. In some cases the bone length can also be calculated from the combined projection image of the femur. It is not possible however to determine the anteversion angle since a view from above onto the femoral head is required for this purpose, as shown in FIG. 3.

A plurality of definitions is used for the femoral anteversion angle. In one definition firstly what is known as the retrocondylar line is determined. The retrocondylar line is the tangent to both condyles at the femoral head. This line is conventionally shown on an osteometric table by the horizontal plane. A further relevant line is the line through the centerpoint of the femoral head and through the centerpoint of the femoral neck. The centerpoint of the maximum anteroposterior thickness of the head of the femur is determined as the centerpoint of the femoral head. The centerpoint of the anteroposterior thickness on the basis of the femoral head is determined as the centerpoint of the femoral neck. The line through the centerpoint of the femoral head and through the centerpoint of the femoral neck runs through the previously determined centerpoint of the femoral head and the centerpoint of the femoral neck. A third relevant line is the line from the front femoral head to the trochanter. This line is located in the plane which runs through the foremost points of the head and the large trochanter.

According to a first definition the anteversion angle is defined as the angle between the line through the centerpoint of the femoral head and through the centerpoint of the femoral neck to the retrocondylar line. According to a second definition the anteversion angle is defined as the angle between the line from the front femoral head to the trochanter to the retrocondylar line.

The anteversion angle can also be defined more generally. The anteversion angle can be produced by way of example by a torsion within the femoral diaphysis. It can also be defined as the angle by which the femoral neck deviates from the frontal plane in a ventral direction. In a newborn the anteversion angle is approximately 30° to 35° and in an adult approximately 10° to 15° (cf. Biomechanik der menschlichen Gelenke [Bio-Mechanics of Human Joints], Paul Klein and Peter Sommerfeld, Elsevier, ISBN: 3-437-55203-1).

FIG. 3 shows a projection image which illustrates the femur 18 from above from the patient's view. The condyle 22 is situated on the femur 18. The line 32 is the retrocondylar line. The line 34 is the line through the centerpoint of the femoral head 36 and through the centerpoint of the femoral neck 38. In the case shown in FIG. 3 the anteversion angle is the angle between the line 34 through the centerpoint of the femoral head 36 and through the centerpoint of the femoral neck 38 to the retrocondylar line 32. As has been mentioned above, other definitions are also possible for the anteversion angle.

The anteversion angle can therefore be determined without the patient being exposed to the radiation of a three-dimensional CT.

Any desired anatomically relevant spacings and angles may be measured instead of the anteversion angle. Any desired angle between bones can be calculated from the three-dimensional volumes which are relevant for an operation. The volume of a healthy body part and the volume of a traumatized body part, by way of example following a fracture, can, moreover, be determined. Geometric relations, by way of example distances and angles, between parts of the body part can be determined within these separate three-dimensional volumes. The traumatized body part can therefore be compared with the healthy body part, whereby the operation can be better prepared for and an improved surgical result is achieved by targeted operations. The position of screws and implants with respect to the body part may also be determined.

The imaging system calculates the reconstructed volume of the femur 16 from the plurality of adjoining and, for the most part, overlapping projection images by means of the above-mentioned algorithms. Projected images can be calculated from this volume which show the femur from a different orientation. The femur can also be examined three-dimensionally. Furthermore, it is possible to calculate and visualize additional sectional images of the bone, in order by way of example to analyze breaks and to examine the positions of implants and screws in order to assess the care of the bone. The patient is exposed to radiation which matches that of conventional two-dimensional imaging. Despite this it is possible by means of the inventive method and the inventive imaging system 26 to reconstruct a three-dimensional volume.

Reference is again made to FIG. 1. The imaging system 26 receives the projection images from the C-arm X-ray system 1 in the form of image data. The imaging system 26 merges the individual projection images to form an overall image. The imaging system 26 also reconstructs the three-dimensional volume.

An operator can visualize details from the combined image, any desired sectional images and/or any desired projection images on the display device 30 by means of an input device 28. The user can also visualize the merged projection image of the entire body part on the display device 30.

The present invention has the advantage that the fields of application of existing X-ray systems are expanded without fundamental changes to the existing X-ray systems being required. The present invention also offers the advantage that by means of two-dimensional imaging by X-ray a volume can be reconstructed without the patient being exposed to the radiation of an additional X-ray by means of a CT. The invention also discloses a simple method for determining the anteversion angle. Furthermore, the present invention enables a more accurate surgical result since, by way of example, breaks may be analyzed better and the anteversion angle can be determined. The inventive method and the inventive imaging system can be used intraoperatively.

Finally reference should be made to the fact that the description of the invention and the exemplary embodiments should basically not be taken to be limiting with respect to a specific physical implementation of the invention. For a person skilled in the art it is in particular obvious that the invention can be implemented in a distributed manner partially or completely using software and/or hardware and/or on a plurality of physical products—in particular also computer program products.

The following is a list of reference numerals used in the above description which may aid the reader in a ready understanding of the invention:

2 C-arm
4 X-ray radiation source
6 X-ray detector
8 carriage
10 holding device
12 operating table
14 patient
16 femur
18 femoral head
22 condyles
24 marking elements
26 imaging system
28 input device
30 display device
32 retrocondylar line
34 line through the centerpoint of the femoral head and through the centerpoint of the femoral neck
36 centerpoint of the femoral head
38 centerpoint of the femoral neck

The invention claimed is:

1. A method of generating a three-dimensional image formation of a body part that is larger than a visual field of an X-ray machine, the method comprising the following steps:

arranging an X-ray source and an X-ray detector at a first position such that the X-ray source and the X-ray detector record a first projection image of at least a first section of a body part;

translating the X-ray source and the X-ray detector to a second position such that the X-ray source and the X-ray detector record a second projection image of at least a second section of the body part, wherein the second section partially overlaps the first section; and reconstructing a three-dimensional volume of the body part from a plurality of projection images including the first projection image and the second projection image using a tomosynthesis algorithm that uses the parallax effect to reconstruct the three-dimensional volume of the body part.

2. The method according to claim 1, which comprises merging the first and second projection images to form one projected image.

3. The method according to claim 1, which comprises the following steps:

producing the plurality of projection images of overlapping sections of the body part at a plurality of positions along a line; and merging the plurality of projection images to form one projected image.

4. The method according to claim 3, wherein the plurality of positions are situated along a straight line.

5. The method according to claim 1, wherein the translating step includes a translatory movement of a C-arm and the X-ray source secured thereto and the X-ray detector secured thereto.

6. The method according to claim 5, wherein the translating step comprises translating the C-arm along a bone axis.

7. The method according to claim 1, which comprises calculating projection geometries for each individual projection image.

8. The method according to claim 1, which comprises the following steps:

detecting projection data of a volume unit of the body part by way of X-ray irradiation from at least two mutually different angles; and reconstructing the volume unit on the basis of the projection images of the volume unit.

9. The method according to claim 8, wherein an emission area of the X-ray source is smaller than a detection area of the X-ray detector, and the method further comprises:

arranging the X-ray source and the X-ray detector at a plurality of positions along a line opposite the volume unit of the body part in such a way that the volume unit is irradiated at different positions from different angles with X-ray radiation emitted by the X-ray source.

10. The method according to claim 1, wherein a calculated projected image is produced from the volume which has a different orientation to the recorded projection images.

11. The method according to claim 1, which comprises at least one of the following steps:

determining a length of a body part from the reconstructed three-dimensional volume of the body part;

determining a bone length from the three-dimensional volume of the body part;

determining a rotation of elements of the body part with respect to each other from the reconstructed three-dimensional volume;

determining a rotation of elements of a bone with respect to each other from the reconstructed three-dimensional volume;

determining axis positions of elements of the body part with respect to each other from the reconstructed three-dimensional volume; or determining the axis positions of elements of a bone with respect to each other from the reconstructed volume data.

12. The method according to claim 1, which comprises using a statistical model to increase an accuracy of the reconstructed three-dimensional volume.

13. The method according to claim 12, which comprises determining an ante-version angle from the volume data and/or at least one calculated projected image.

14. The method according to claim 1, wherein the body part is a bone.

15. The method according to claim 14, wherein the body part is a femur.

16. An imaging system configured for carrying out the steps of the method according to claim 1.

17. A C-arm X-ray system, comprising an imaging system configured for carrying out the steps of the method according to claim 1.

18. A computer program product stored in non-transitory form, loadable or loaded into a memory of a computer which, upon being programmed, is configured to perform at least one of the steps of the method according to claim 1.

* * * * *